United States Patent
Kosaka et al.

(10) Patent No.: US 9,981,073 B2
(45) Date of Patent: May 29, 2018

(54) SURFACE-MODIFIED METAL AND METHOD FOR MODIFYING METAL SURFACE

(71) Applicant: SUMITOMO RUBBER INDUSTRIES, LTD., Kobe-shi, Hyogo (JP)

(72) Inventors: Shunsuke Kosaka, Kobe (JP); Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 0 days. days.

(21) Appl. No.: 15/201,963

(22) Filed: Jul. 5, 2016

(65) Prior Publication Data
US 2017/0035944 A1 Feb. 9, 2017

(30) Foreign Application Priority Data
Aug. 3, 2015 (JP) .................................. 2015-153488

(51) Int. Cl.
| | |
|---|---|
| *C08F 2/46* | (2006.01) |
| *C08F 2/50* | (2006.01) |
| *C08G 61/04* | (2006.01) |
| *A61L 31/10* | (2006.01) |
| *A61L 29/08* | (2006.01) |
| *A61L 29/14* | (2006.01) |
| *A61L 31/14* | (2006.01) |
| *A61L 31/02* | (2006.01) |
| *C08F 220/34* | (2006.01) |
| *C08F 220/38* | (2006.01) |
| *C08F 220/56* | (2006.01) |
| *C23C 26/00* | (2006.01) |

(52) U.S. Cl.
CPC ............. *A61L 31/10* (2013.01); *A61L 29/085* (2013.01); *A61L 29/14* (2013.01); *A61L 31/022* (2013.01); *A61L 31/14* (2013.01); *C08F 220/34* (2013.01); *C08F 220/38* (2013.01); *C08F 220/56* (2013.01); *C23C 26/00* (2013.01); *A61L 2400/10* (2013.01); *A61L 2420/00* (2013.01); *A61L 2420/02* (2013.01)

(58) Field of Classification Search
CPC .... A61L 31/10; A61L 31/022; A61L 2420/00; A61L 2420/02; A61L 31/14; A61L 2400/10; A61L 29/14; A61L 29/085; C08F 220/38; C08F 220/56; C08F 220/34; C08L 33/10; C08L 33/08; C23C 26/00
USPC ........... 522/55, 49, 6, 71, 189, 184, 1; 520/1
See application file for complete search history.

(56) References Cited

U.S. PATENT DOCUMENTS

| | | | |
|---|---|---|---|
| 3,532,655 A | 10/1970 | Radlove et al. | |
| 6,391,463 B1 | 5/2002 | Fan et al. | |
| 9,695,331 B2 | 7/2017 | Horgan et al. | |
| 2003/0215649 A1* | 11/2003 | Jelle ........................ | A61L 27/34 428/447 |
| 2009/0171302 A1 | 7/2009 | Eramo, Jr. et al. | |
| 2009/0176183 A1* | 7/2009 | Conrad ..................... | A61C 7/20 433/20 |
| 2011/0059874 A1 | 3/2011 | Rooijmans et al. | |
| 2011/0212152 A1 | 9/2011 | Ditizio et al. | |
| 2012/0059111 A1 | 3/2012 | Sandhu et al. | |
| 2013/0242467 A1 | 9/2013 | Biler | |
| 2013/0266815 A1* | 10/2013 | Horgan ................ | C09D 133/14 428/447 |
| 2016/0008520 A1* | 1/2016 | Minagawa ............... | C09D 4/00 428/35.8 |
| 2016/0159019 A1 | 6/2016 | Bruce et al. | |
| 2016/0184487 A1 | 6/2016 | Minagawa | |
| 2017/0056563 A1* | 3/2017 | Minagawa ............ | A61L 31/022 |

FOREIGN PATENT DOCUMENTS

| | | |
|---|---|---|
| CN | 101970583 A | 2/2011 |
| CN | 103209717 A | 7/2013 |
| GB | 1065031 A | 4/1967 |
| JP | 5-269919 A | 10/1983 |
| JP | 60-179204 A | 9/1985 |
| JP | 62-52562 A | 3/1987 |
| JP | 2-40322 A | 2/1990 |
| JP | 4-357951 A | 12/1992 |
| JP | 4-362104 A | 12/1992 |
| JP | 6-510322 A | 11/1994 |
| JP | 8-325524 A | 12/1996 |
| JP | 2001-29452 A | 2/2001 |
| JP | 2005-528253 A | 9/2005 |
| JP | 2011-513566 A | 4/2011 |

(Continued)

OTHER PUBLICATIONS

International Search Report and Written Opinion of the International Searching Authority (Forms PCT/ISA/237 and PCT/ISA/210), dated Dec. 22, 2014, for International Application No. PCT/JP2014/076893, with an English translation of the Search Report.

*Primary Examiner* — Jessica Whiteley
(74) *Attorney, Agent, or Firm* — Birch, Stewart, Kolasch & Birch, LLP

(57) ABSTRACT

Provided are surface-modified metals such as metal medical devices, e.g. guide wires, syringe needles, and metal tubes in medical devices or equipment, and methods for modifying a metal surface, wherein a lubricant layer is firmly bonded to the metal surface to impart lubricity to the metal surface and further to improve the durability of the lubricant layer on the metal surface, thereby suppressing deterioration of the sliding properties. Included is a surface-modified metal at least partially having a treated surface, the treated surface being obtained by treating a surface of a metal with a silane coupling agent, followed by adsorbing a hydrogen abstraction type photopolymerization initiator onto the surface and then polymerizing a monomer in the presence of an alkali metal salt.

13 Claims, No Drawings

(56) References Cited

FOREIGN PATENT DOCUMENTS

| | | |
|---|---|---|
| WO | WO 03/097117 A1 | 11/2003 |
| WO | WO 2005/081840 A2 | 9/2005 |
| WO | WO 2006/056482 A1 | 6/2006 |
| WO | WO 2012/032283 A1 | 3/2012 |

* cited by examiner

SURFACE-MODIFIED METAL AND METHOD FOR MODIFYING METAL SURFACE

TECHNICAL FIELD

The present invention relates to surface-modified metals and methods for modifying a metal surface.

BACKGROUND ART

Guide wires and other tools used for assisting insertion of medical devices such as catheters into the body are inserted into and optionally placed in blood vessels, respiratory tracts, urethra, and other body cavities or tissues. When a medical device such as a catheter or guide wire is inserted into the body, the medical device may damage the tissue or the like in the body and produce inflammation or cause pain to the patient. To ameliorate these problems, it has been desired to improve the sliding properties of the medical devices intended to be inserted into the body.

To ameliorate the above problems, a method has been proposed in which the surface of a medical device such as a catheter or guide wire is coated with a hydrophilic resin, a fluororesin, or the like.

Moreover, the insertion of a syringe needle into the body may also damage the tissue or the like in the body and cause pain to the patient. Furthermore, if the inner surface of a syringe needle, a metal tube in a medical device or equipment, or other metal devices exhibits reduced lubricity when wetted, there may be difficulties in rapidly and accurately delivering chemicals or blood. Accordingly, it has also been desired to improve and maintain the lubricity of the inner surface of these devices when wetted.

As described above, there have been needs to improve the sliding properties of medical devices and syringe needles, and to improve and maintain the lubricity of the inner surface of syringe needles, metal tubes in medical devices or equipment, or other metal devices when wetted. Various methods have therefore been tried to impart lubricity to the surface of medical devices such as catheters or guide wires to improve the sliding properties thereof.

However, all these methods only allow the surface of medical devices to be coated with a resin or to be cured after the coating. Especially in cases where the surface of the medical device is made of a metal, the coating resin, which is not firmly bonded to the surface of the medical device, is easily peeled or removed from the surface of the medical device, unfortunately resulting in reduction in the sliding properties of the medical device. Accordingly, there is a need for the development of metal medical devices that exhibit reduced deterioration in sliding properties. In addition, there is still room for improvement in enhancing and maintaining the lubricity of the inner surface of syringe needles, metal tubes in medical devices or equipment, or other metal devices when wetted.

SUMMARY OF INVENTION

Technical Problem

The present invention aims to solve the above problems and provide surface-modified metals such as metal medical devices, e.g. guide wires, syringe needles, and metal tubes in medical devices or equipment, and methods for modifying a metal surface, wherein a lubricant layer is firmly bonded to the metal surface to impart lubricity to the metal surface and further to improve the durability of the lubricant layer on the metal surface, thereby suppressing deterioration of the sliding properties.

Solution to Problem

The present invention relates to a surface-modified metal, at least partially having a treated surface, the treated surface being obtained by treating a surface of a metal with a silane coupling agent, followed by adsorbing a hydrogen abstraction type photopolymerization initiator onto the surface and then polymerizing a monomer in the presence of an alkali metal salt.

Preferably, the treated surface is obtained by, after adsorbing the hydrogen abstraction type photopolymerization initiator onto the surface and then polymerizing the monomer in the presence of the alkali metal salt, further performing the following step at least once: polymerizing a monomer in the presence of a hydrogen abstraction type photopolymerization initiator and an alkali metal salt; or adsorbing a hydrogen abstraction type photopolymerization initiator onto the surface and then polymerizing a monomer in the presence of an alkali metal salt.

The present invention relates to a surface-modified metal, at least partially having a treated surface, the treated surface being obtained by treating a surface of a metal with a silane coupling agent, followed by polymerizing a monomer in the presence of a hydrogen abstraction type photopolymerization initiator and an alkali metal salt.

Preferably, the treated surface is obtained by, after polymerizing the monomer in the presence of the hydrogen abstraction type photopolymerization initiator and the alkali metal salt, further performing the following step at least once: polymerizing a monomer in the presence of a hydrogen abstraction type photopolymerization initiator and an alkali metal salt; or adsorbing a hydrogen abstraction type photopolymerization initiator onto the surface and then polymerizing a monomer in the presence of an alkali metal salt.

The monomer is preferably at least one selected from the group consisting of hydrophilic monomers, alkali metal-containing monomers, and halogen-containing monomers.

The silane coupling agent is preferably a vinyl group-containing compound.

The metal to be treated is preferably stainless steel or a nickel-titanium alloy.

The present invention relates to a medical device, including the surface-modified metal.

The medical device is preferably a guide wire, a syringe needle, or a tube of a medical instrument.

The present invention relates to a method for modifying a metal surface, the method including:
step 1 of treating a metal surface with a silane coupling agent;
step 2 of adsorbing a hydrogen abstraction type photopolymerization initiator onto the metal surface treated in the step 1 to form polymerization initiation points; and
step 3 of polymerizing a monomer starting from the polymerization initiation points in the presence of an alkali metal salt to grow polymer chains on the metal surface.

The present invention relates to a method for modifying a metal surface, the method including:
step I of treating a metal surface with a silane coupling agent; and
step II of polymerizing a monomer in the presence of a hydrogen abstraction type photopolymerization initiator and an alkali metal salt on the metal surface treated in the step I to grow polymer chains on the metal surface.

Preferably, after the step 3 or the step II, the method for modifying a metal surface includes performing, at least once: a step of adsorbing a hydrogen abstraction type photopolymerization initiator onto the surface and then polymerizing a monomer in the presence of an alkali metal salt; or a step of polymerizing a monomer in the presence of a hydrogen abstraction type photopolymerization initiator and an alkali metal salt.

Advantageous Effects of Invention

The surface-modified metals of the present invention are characterized by at least partially having a treated surface obtained by treating the surface of metals with a silane coupling agent, followed by adsorbing a hydrogen abstraction type photopolymerization initiator onto the surface and then polymerizing a monomer in the presence of an alkali metal salt; or a treated surface obtained by treating the surface of metals with a silane coupling agent, followed by polymerizing a monomer in the presence of a hydrogen abstraction type photopolymerization initiator and an alkali metal salt. Such surface-modified metals have lubricity imparted to the metal surface, and further have improved durability of the lubricant layer on the surface and therefore reduced deterioration in the sliding properties of the metal. In addition, the efficiency of the polymerization is improved. These effects are presumably produced by the presence of a hydrogen abstraction type photopolymerization initiator that allows a polymer derived from a monomer to be chemically bonded to the metal surface, and an alkali metal salt that promotes the polymerization so that the polymerization can be completed in a shorter time.

DESCRIPTION OF EMBODIMENTS

The first surface-modified metal of the present invention is characterized by at least partially having a treated surface obtained by treating the surface of a metal with a silane coupling agent, followed by adsorbing a hydrogen abstraction type photopolymerization initiator onto the surface and then polymerizing a monomer in the presence of an alkali metal salt.

Lubricant layers formed on metal surfaces by conventional surface treatment or coating methods are not chemically bonded to the metal surfaces and are easily peeled or removed by a stress such as rubbing by a hand, friction with an object contacting the metal (e.g., a catheter or cells in the body when the metal is a guide wire), flows of chemicals or blood, or other causes. Such lubricant layers are therefore disadvantageous in terms of durability or maintaining sliding properties. In contrast, the surface-modified metal of the present invention is obtained by polymerizing a monomer in the presence of a hydrogen abstraction type photopolymerization initiator and an alkali metal salt which allow a polymer derived from the monomer to be chemically bonded to the metal surface and, further, promote the polymerization rate. Thus, a lubricant layer is formed by the efficient surface treatment, and further the formed lubricant layer is inhibited from being peeled or removed by a stress, friction, liquid flows, or other causes and thus deterioration in the sliding properties of the metal is prevented.

The surface-modified metal of the present invention may be prepared by, for example, a method for modifying a metal surface which includes: step 1 of treating a metal surface with a silane coupling agent; step 2 of adsorbing a hydrogen abstraction type photopolymerization initiator onto the metal surface treated in the step 1 to form polymerization initiation points; and step 3 of polymerizing a monomer starting from the polymerization initiation points in the presence of an alkali metal salt to grow polymer chains on the metal surface.

By the treatment with a silane coupling agent before the polymerization of a monomer in the presence of a hydrogen abstraction type photopolymerization initiator and an alkali metal salt, the polymer is chemically bonded to the metal via the silane coupling agent so that a stronger bond is formed. Thus, the surface-modified metal has further enhanced and more durable sliding properties.

Examples of the metal include, but are not limited to, stainless steel, nickel-titanium alloys, iron, titanium, aluminum, tin, and zinc-tungsten alloys. Among these, stainless steel or nickel-titanium alloys are preferred in view of bonding between the metal surface and the lubricant layer and biocompatibility.

The silane coupling agent may suitably be a vinyl group-containing compound. For example, for easy hydrogen abstraction, the vinyl group-containing compound preferably contains a hydrolyzable group and a vinyl group. Such a vinyl group-containing compound reacts with and bonds to the hydroxy group on the metal surface via the hydrolyzable group, and its vinyl group can form a polymerization initiation point for monomers. Consequently, polymer chains grown starting from the polymerization initiation points are chemically bonded to the metal via the silane coupling agent.

Preferred as the silane coupling agent are vinyltrimethoxysilane, vinyltriethoxysilane, (3-acryloyloxypropyl)trimethoxysilane, (3-acryloyloxypropyl)triethoxysilane, (3-methacryloyloxypropyl)trimethoxysilane, (3-methacryloyloxypropyl)triethoxysilane, vinylchlorodimethylsilane, (3-acryloyloxypropyl)chlorodimethylsilane, and (3-methacryloyloxypropyl)chlorodimethylsilane. More preferred are (3-acryloyloxypropyl)trimethoxysilane, (3-acryloyloxypropyl)triethoxysilane, and (3-acryloyloxypropyl)chlorodimethylsilane. In view of reactivity or safety, particularly preferred is (3-acryloyloxypropyl)trimethoxysilane.

The treatment with the silane coupling agent may be carried out by any method that allows the silane coupling agent to be brought into contact with the metal, such as by coating it by for example application, spraying, or immersion. The treatment is preferably carried out by preparing a solution (e.g. an aqueous solution, alcohol solution, or acetone solution) of a silane coupling agent (silane compound), and coating the metal surface with the solution, followed either by drying by heat, or by standing under air moisture, wet or other conditions to cause hydrolysis and dehydration condensation. According to these methods, a chemical bond is formed between the hydroxy group on the metal surface and the silane coupling agent (silane compound) so that the silane coupling agent is fixed. The drying temperature and drying time may be selected appropriately, for example, to allow formation of a chemical bond. The drying temperature is preferably 40° C. to 150° C. In the preparation of the aqueous solution, an additional operation may be performed as appropriate, for example, by adding alcohol to prepare a mixed water/alcohol solution or by adjusting the pH to weakly acidic with acetic acid or other acids. This is because the solubility of the silane coupling agent in water varies depending on the type of silane coupling agent.

The formation of polymerization initiation points in step 2 may be carried out, for example, by adsorbing a hydrogen abstraction type photopolymerization initiator onto the metal surface treated with a silane coupling agent in step 1, to form polymerization initiation points, or by adsorbing a hydrogen abstraction type photopolymerization initiator onto the metal surface treated with a silane coupling agent and then irradiating the surface with ultraviolet light having a wavelength of 300 to 400 nm to form polymerization initiation points from the hydrogen abstraction type photopolymerization initiator on the surface.

Examples of the hydrogen abstraction type photopolymerization initiator include carbonyl compounds, organic sulfur compounds such as tetraethylthiuram disulfide, persulfides, redox compounds, azo compounds, diazo compounds, halogen compounds, and photoreducing dyes. Preferred among these are carbonyl compounds.

The carbonyl compound used as a hydrogen abstraction type photopolymerization initiator is preferably benzophenone or a derivative thereof (a benzophenone compound). For example, it may suitably be a benzophenone compound represented by the following formula:

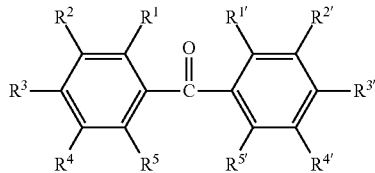

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxy group, a primary, secondary, or tertiary amino group, a mercapto group, or a hydrocarbon group that may contain an oxygen, nitrogen, or sulfur atom, and any two adjacent groups of $R^1$ to $R^5$ and $R^{1'}$ to $R^{5'}$ may be joined to each other to form a ring together with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone as these compounds contribute to forming polymer brushes well.

The hydrogen abstraction type photopolymerization initiator may also suitably be a thioxanthone compound because it provides a high polymerization rate and because of its ease of adsorption and/or reaction. For example, it may suitably be a compound represented by the following formula:

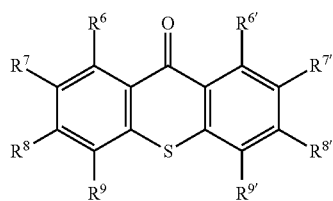

wherein $R^6$ to $R^9$ and $R^{6'}$ to $R^{9'}$ are the same as or different from one another and each represent a hydrogen atom, a halogen atom, or an alkyl, cyclic alkyl, aryl, alkenyl, alkoxy, or aryloxy group.

Examples of the thioxanthone compound represented by the above formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, and 2-p-octyloxyphenyl-4-ethylthioxanthone. Preferred among these are those which are substituted at one or two, especially two, of $R^6$ to $R^9$ and $R^{6'}$ to $R^{9'}$ with alkyl groups. More preferred is 2,4-diethylthioxanthone.

The adsorption of a hydrogen abstraction type photopolymerization initiator such as a benzophenone or thioxanthone compound onto the metal surface may be carried out as follows. In the case of a benzophenone or thioxanthone compound, for example, the benzophenone or thioxanthone compound is dissolved in an organic solvent to prepare a solution; a surface portion of the metal to be modified is treated with this solution so that the compound is adsorbed on the surface portion; and, if necessary, the organic solvent is dried and evaporated off, whereby polymerization initiation points are formed. The surface-treating method may be any method that allows the solution of the benzophenone or thioxanthone compound to be brought into contact with the metal surface treated with a silane coupling agent. Suitable methods include applying or spraying the benzophenone or thioxanthone compound solution onto the surface; or immersing the surface into the solution. When only a part of the surface needs to be modified, it is sufficient to adsorb the hydrogen abstraction type photopolymerization initiator only onto the necessary part of the surface. In this case, for example, application or spraying of the solution is suitable. Examples of the solvent include methanol, ethanol, acetone, benzene, toluene, methyl ethyl ketone, ethyl acetate, and THF. Preferred is acetone because it dries and evaporates quickly.

As described above, after a hydrogen abstraction type photopolymerization initiator is adsorbed on the metal surface treated with a silane coupling agent, the metal surface may further be irradiated with ultraviolet light having a wavelength of 300 to 400 nm to form polymerization initiation points from the hydrogen abstraction type photopolymerization initiator on the surface. This ultraviolet irradiation may be carried out by known methods. For example, the ultraviolet irradiation may be carried out in the same manner as described later. In the adsorption of the photopolymerization initiator and the fixation thereof by ultraviolet irradiation (chemical bond formation), hydrogen is abstracted from the hydroxy group on the metal surface and the resulting hydroxy group on the metal surface is covalently bonded to the carbon of C=O in the benzophenone or thioxanthone compound while the abstracted hydrogen is bonded to the oxygen of C=O to form C—O—H.

Step 3 may be carried out, for example, by radically polymerizing a monomer starting from the polymerization initiation points formed in step 2, by irradiation with ultraviolet light having a wavelength of 300 to 400 nm in the presence of an alkali metal salt to grow polymer chains on the metal surface. In particular, by carrying out step 3 in the presence of an alkali metal salt, the polymer is sufficiently fixed to the metal surface, and therefore excellent lubricity and excellent lubricant durability are imparted to the metal surface.

Examples of alkali metal salts that can be used include halogenated alkali metal salts, alkali metal carbonates, alkali metal bicarbonates, alkali metal hydrogen carbonates, alkali metal nitrates, alkali metal sulfates, alkali metal bisulfates, alkali metal phosphates, alkali metal hydroxides, alkali metal acetates, alkali metal citrates, and alkali metal lactates. The alkali metal salt may be a water-soluble lithium, sodium, potassium, rubidium, or cesium salt.

Specific examples include sodium chloride, potassium chloride, cesium chloride, sodium bromide, potassium bromide, sodium nitrate, potassium nitrate, sodium carbonate, potassium carbonate, sodium sulfate, potassium sulfate, sodium bisulfate, potassium bisulfate, sodium phosphate, potassium phosphate, sodium hydroxide, potassium hydroxide, sodium hydrogen carbonate, sodium dihydrogen phosphate, disodium hydrogen phosphate, trisodium phosphate, sodium acetate, potassium acetate, sodium citrate, potassium citrate, sodium lactate, and potassium lactate. The alkali metal salts may be used alone or in combinations of two or more.

In view of lubricity and lubricant durability, halogenated alkali metal salts are preferred among these, and sodium chloride or potassium chloride is particularly preferred.

Suitable examples of the monomer include hydrophilic monomers, alkali metal-containing monomers (monomers each containing an alkali metal in the molecule), zwitterionic monomers (zwitterionic group-containing compounds: compounds each bearing a center of permanent positive charge and a center of negative charge), and halogen-containing monomers (monomers each containing a halogen in the molecule). If monomers simultaneously correspond to two or more of the above types of monomers, i.e. hydrophilic monomers, alkali metal-containing monomers, zwitterionic monomers, and halogen-containing monomers, as in the case of, for example, a monomer containing an alkali metal and a halogen (corresponding to both the alkali metal-containing monomer type and the halogen-containing monomer type), they are included in any of the two or more monomer types. The monomers may be used alone or in combinations of two or more.

The hydrophilic monomer may be a monomer containing a functional group that can be converted to a hydrophilic functional group, and examples include monomers containing hydrophilic groups, such as typically an amide group, a sulfuric acid group, a sulfonic acid group, a carboxylic acid group, a hydroxy group, an amino group, an oxyethylene group, or precursor functional groups of these groups.

Specific examples of the hydrophilic monomer include (meth)acrylic acid, (meth)acrylic acid esters such as methoxyethyl (meth)acrylate and hydroxyethyl (meth)acrylate, alkali metal salts of (meth)acrylic acid, and amine salts of (meth)acrylic acid. Monomers containing a C—N bond in the molecule may also be mentioned. Examples of the monomer containing a C—N bond in the molecule include (meth) acrylamide; N-alkyl-substituted (meth)acrylamide derivatives such as N-ethyl(meth)acrylamide, N-n-propyl (meth)acrylamide, N-isopropyl(meth)acrylamide, N-cyclopropyl(meth)acrylamide, N-methoxyethyl(meth)acrylamide, and N-ethoxyethyl(meth)acrylamide; N,N-dialkyl-substituted (meth)acrylamide derivatives such as N,N-dimethyl(meth)acrylamide, N,N-ethylmethyl(meth)acrylamide, and N,N-diethyl(meth)acrylamide; hydroxy (meth)acrylamide; hydroxy(meth)acrylamide derivatives such as N-hydroxyethyl(meth)acrylamide; and cyclic group-containing (meth)acrylamide derivatives such as (meth) acryloylmorpholine. Preferred among these are (meth) acrylic acid, (meth)acrylic acid esters, alkali metal salts of (meth)acrylic acid, amine salts of (meth)acrylic acid, acrylonitrile, (meth)acrylamide, dimethyl(meth)acrylamide, diethyl(meth)acrylamide, isopropyl(meth)acrylamide, hydroxyethyl(meth)acrylamide, methoxyethyl(meth)acrylamide, and (meth)acryloylmorpholine. More preferred is (meth) acrylamide or 2-methoxyethyl acrylate, with 2-methoxyethyl acrylate being particularly preferred.

Examples of the alkali metal-containing monomer include alkali metal salts of acrylic acid such as sodium acrylate and potassium acrylate; alkali metal salts of methacrylic acid such as sodium methacrylate and potassium methacrylate; alkali metal salts of itaconic acid such as sodium itaconate and potassium itaconate; alkali metal salts of 3-vinylpropionic acid such as sodium 3-vinylpropionate and potassium 3-vinylpropionate; alkali metal salts of vinylsulfonic acid such as sodium vinylsulfonate and potassium vinylsulfonate; alkali metal salts of 2-sulfoethyl (meth)acrylate such as sodium 2-sulfoethyl (meth)acrylate and potassium 2-sulfoethyl (meth)acrylate; alkali metal salts of 3-sulfopropyl (meth) acrylate such as sodium 3-sulfopropyl (meth) acrylate and potassium 3-sulfopropyl (meth)acrylate; alkali metal salts of 2-acrylamide-2-methylpropanesulfonic acid such as sodium 2-acrylamide-2-methylpropanesulfonate and potassium 2-acrylamide-2-methylpropanesulfonate; and alkali metal salts of styrenesulfonic acid such as sodium styrenesulfonate and potassium styrenesulfonate. Preferred among these is potassium 3-sulfopropyl methacrylate.

Examples of the zwitterionic monomer include carboxybetaines, sulfobetaines, and phosphobetaines. Other examples include compounds represented by the formula (1) below, suitably compounds represented by the formula (2) below.

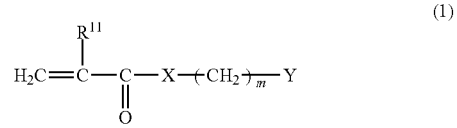

(1)

In the formula, $R^{11}$ represents —H or —CH$_3$; X represents —O—, —NH— or —N$^+$—; m represents an integer of 1 or more; and Y represents a zwitterionic group or a halogen group such as Cl$^-$, Br$^-$, or F$^-$.

In the formula (1), preferably, $R^{11}$ is —CH$_3$, X is —O—, and m is an integer of 1 to 10. In the zwitterionic group designated by Y, the cation may be a quaternary ammonium such as tetraalkylammonium, and the anion may be a carboxylate, sulfonate, or phosphate.

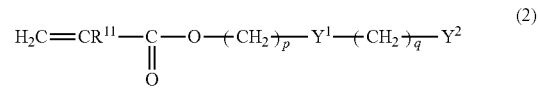

(2)

In the formula, $R^{11}$ represents —H or —CH$_3$; p and q each represent an integer of 1 or more; and $Y^1$ and $Y^2$ represent ionic functional groups having electric charges opposite to each other.

In the formula (2), p is preferably an integer of 2 or larger, more preferably an integer of 2 to 10, and q is preferably an integer of 1 to 10, more preferably an integer of 2 to 4. Preferred examples of $R^{11}$ are the same as mentioned above. The symbols $Y^1$ and $Y^2$ are as described for the cation and anion above.

Typical suitable examples of the zwitterionic monomer include compounds represented by the following formulas (2-1) to (2-4):

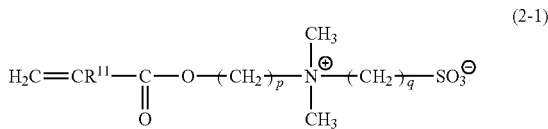

(2-1)

wherein $R^{11}$ represents a hydrogen atom or a methyl group, and p and q each represent an integer of 1 to 10,

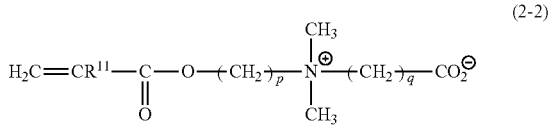

(2-2)

p and q each represent an integer of 1 to 10,

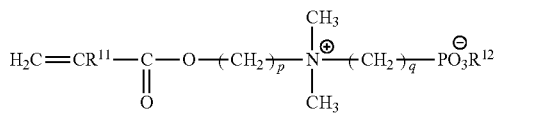

(2-3)

wherein $R^{11}$ represents a hydrogen atom or a methyl group; $R^{12}$ represents a C1-C6 hydrocarbon group; and p and q each represent an integer of 1 to 10,

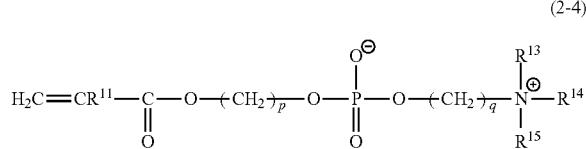

(2-4)

wherein $R^{11}$ represents a hydrogen atom or a methyl group; $R^{13}$, $R^{14}$, and $R^{15}$ are the same as or different from one another and each represent a C1-C2 hydrocarbon group; and p and q each represent an integer of 1 to 10.

Examples of compounds represented by the formula (2-1) include dimethyl(3-sulfopropyl) (2-(meth)acryloyloxyethyl)-ammonium betaine and [2-(methacryloyloxy)ethyl]dimethyl-(3-sulfopropyl)aminium hydroxide. Examples of compounds represented by the formula (2-2) include dimethyl(2-carboxyethyl) (2-(meth)acryloyloxyethyl)ammonium betaine. Examples of compounds represented by the formula (2-3) include dimethyl(3-methoxyphosphopropyl)-(2-(meth)acryloyloxyethyl)ammonium betaine. Examples of compounds represented by the formula (2-4) include 2-(meth)acryloyloxyethyl phosphorylcholine. Other zwitterionic monomers include 2-(meth)acryloyloxyethyl carboxybetaine and 2-(meth)acryloyloxyethyl sulfobetaine. Preferred among these is 2-(meth)acryloyloxyethyl phosphorylcholine because of its high biocompatibility, i.e. low protein adsorbability.

The halogen-containing monomer refers to a hydrophilic monomer containing a halogen atom in the molecule. The halogen-containing monomers may be used alone or in combinations of two or more.

In view of lubricity and lubricant durability, the halogen-containing monomer may suitably be a nitrogen-containing monomer (halogen- and nitrogen-containing monomer). Specific preferred examples of such monomers include compounds represented by the following formula (I):

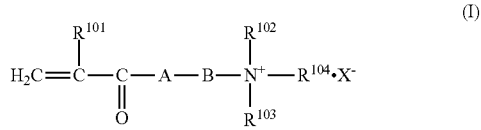

(I)

wherein A represents an oxygen atom or NH; B represents a C1-C4 alkylene group; $R^{101}$ represents a hydrogen atom or a methyl group; $R^{102}$, $R^{103}$, and $R^{104}$ are the same as or different from one another and each represent a C1-C4 alkyl group; and $X^-$ represents a halogen ion.

The symbol A is preferably an oxygen atom. The symbol B may be a linear or branched alkylene group such as a methylene group, an ethylene group, or a propylene group, with a methylene group or an ethylene group being preferred. Each of $R^{102}$ to $R^{104}$ may be a linear or branched alkyl group such as a methyl group, an ethyl group, or a propyl group, with a methyl group or an ethyl group being preferred. The symbol X (halogen atom) may be, for example, fluorine, chlorine, or bromine, preferably chlorine.

Examples of nitrogen-containing monomers represented by the formula (I) include 2-(methacroyloxy)ethyl trimethylammonium chloride (2-(methacroyloxy)ethyl trimethylaminium chloride), 2-(acryloyloxy)ethyl trimethylammonium chloride (2-(acryloyloxy)ethyl trimethylaminium chloride), 2-(methacroyloxy)ethyl dimethylethylammonium chloride (2-(methacroyloxy)ethyl dimethylethylaminium chloride), and 2-(acryloyloxy)ethyl dimethylethylammonium chloride (2-(acryloyloxy)ethyl dimethylethylaminium chloride).

The radical polymerization of a monomer in step 3 is carried out, for example, as follows: a solution of an alkali metal salt and a monomer or a mixture of an alkali metal salt and a liquid monomer is applied (sprayed) onto the silane coupling agent-treated metal surface on which a benzophenone or thioxanthone compound or the like has been adsorbed, or the silane coupling agent-treated metal is immersed in a solution of an alkali metal salt and a monomer or a mixture of an alkali metal salt and a liquid monomer; and then the metal surface is irradiated with ultraviolet light to allow radical polymerization (photoradical polymerization) of the monomer to proceed, whereby polymer chains are grown on the metal surface. After the application, the metal surface may further be covered with a transparent cover of glass, PET, polycarbonate or other materials, followed by irradiating the covered surface with light (e.g. ultraviolet light) to allow radical polymerization (photoradical polymerization) of the monomer to proceed, whereby polymer chains are grown on the metal surface.

The solvent for application (spraying), the method for application (spraying), the method for immersion, the conditions for irradiation, and the like may be conventionally known materials or methods. The solution of the radically polymerizable monomer may be an aqueous solution, or a solution in an organic solvent that does not dissolve the hydrogen abstraction type photopolymerization initiator used (e.g. a benzophenone or thioxanthone compound). Moreover, the solution of the radically polymerizable monomer or the liquid radically polymerizable monomer may contain a known polymerization inhibitor such as 4-methylphenol.

In the present invention, the radical polymerization of the monomer is allowed to proceed by light irradiation after the application of the monomer solution or the liquid monomer, or after the immersion in the monomer solution or the liquid monomer. In the light irradiation, ultraviolet light sources with an emission wavelength mainly in the ultraviolet region, such as high-pressure mercury lamps, metal halide lamps, and LED lamps, can be suitably used. The light dose may be selected appropriately in view of polymerization time and uniform progress of the reaction. Moreover, in order to prevent inhibition of polymerization due to active gas such as oxygen in the reaction vessel and the reaction pipe, oxygen is preferably removed from the reaction vessel, the reaction pipe, and the reaction solution during or before the light irradiation. To this end, appropriate operations may be performed; for example, an inert gas such as nitrogen gas or argon gas is introduced into the reaction vessel, the reaction pipe, and the reaction solution to discharge active gas such as oxygen from the reaction system and replace the atmosphere in the reaction system with the inert gas. Furthermore, in order to prevent inhibition of the reaction due to oxygen and the like, for example, a measure may also appropriately be taken in which an ultraviolet light source is placed such that an air layer (oxygen content: 15% or higher) does not exist between the reaction vessel made of glass, plastic or the like and the reaction solution or the object intended to be modified.

The ultraviolet light preferably has a wavelength of 300 to 400 nm. Such a wavelength enables polymer chains to be formed well on the metal surface. Examples of light sources that can be used include high-pressure mercury lamps, LEDs with a center wavelength of 365 nm, LEDs with a center wavelength of 375 nm, and LEDs with a center wavelength of 385 nm. More preferred is irradiation with LED light having a wavelength of 355 to 390 nm. In particular, for example, LEDs with a center wavelength of 365 nm, which is close to the excitation wavelength (366 nm) of benzophenone, are preferred in view of efficiency. Light having a wavelength of less than 300 nm can cleave and damage molecules of the object intended to be modified. For this reason, light having a wavelength of 300 nm or greater is preferred. More preferred is light having a wavelength of 355 nm or greater because it produces very little damage to the metal. In contrast, light having a wavelength of greater than 400 nm is less likely to activate the photopolymerization initiator, so that the polymerization reaction does not readily proceed. For this reason, light having a wavelength of 400 nm or less is preferred. Although LED light is suitable because the wavelength range of LED light is narrow so that no wavelengths other than the center wavelength are emitted, a mercury lamp or the like can also achieve similar effects to those of LED light if a filter is used to block light with wavelengths less than 300 nm.

In the present invention, polymer chains can be produced with good productivity by reducing the duration of irradiation with ultraviolet light having a wavelength of, for example, 300 to 400 nm. For example, when polymer chains are formed on a metal plate, the duration of light irradiation for one polymer chain forming step may be 3 to 120 minutes, and can also be reduced to 5 to 100 minutes, or 10 to 80 minutes. When polymer chains are formed on a guide wire, the duration of light irradiation for one polymer chain forming step may be 10 to 1,000 minutes, and can also be reduced to 60 to 800 minutes, or 100 to 600 minutes.

The second surface-modified metal of the present invention is characterized by at least partially having a treated surface obtained by treating the surface of a metal with a silane coupling agent, followed by polymerizing a monomer in the presence of a hydrogen abstraction type photopolymerization initiator and an alkali metal salt. Such a surface-modified metal may be prepared by, for example, a method for modifying a metal surface which includes: step I of treating a metal surface with a silane coupling agent; and step II of polymerizing a monomer in the presence of a hydrogen abstraction type photopolymerization initiator and an alkali metal salt on the metal surface treated in the step I to grow polymer chains on the metal surface. By radically polymerizing a monomer in the presence of a hydrogen abstraction type photopolymerization initiator as an initiator and further an alkali metal salt to produce polymer chains, a surface-modified metal can be produced on which a polymer layer (polymer) is fixed to the metal surface. Thus, similarly to the above, a lubricant layer is formed by the efficient surface treatment, and further the formed lubricant layer is inhibited from being peeled or removed by a stress, friction, liquid flows, or other causes and thus deterioration in the sliding properties of the metal is prevented. The metal, the silane coupling agent, the hydrogen abstraction type photopolymerization initiator, the alkali metal salt, and the monomer used in step I may be the same as those described above.

The treatment with a silane coupling agent in step I may be carried out in the same manner as in step 1.

Step II may be carried out, for example, by bringing the metal surface treated with a silane coupling agent into contact with a hydrogen abstraction type photopolymerization initiator, an alkali metal salt, and a monomer, followed by irradiating the metal surface with LED light having a wavelength of 300 to 400 nm to form polymerization initiation points from the photopolymerization initiator while radically polymerizing the monomer starting from the polymerization initiation points in the presence of the alkali metal salt to grow polymer chains.

The radical polymerization of a monomer in step II may be carried out as follows: a solution of a monomer or a liquid monomer which contains a hydrogen abstraction type photopolymerization initiator such as a benzophenone or thioxanthone compound and an alkali metal salt is applied (sprayed) onto the metal surface treated with a silane coupling agent, or the metal surface treated with a silane coupling agent is immersed in a solution of a monomer or a liquid monomer which contains a hydrogen abstraction type photopolymerization initiator and an alkali metal salt; and then the metal surface is irradiated with light (e.g. ultraviolet light) to allow radical polymerization (photoradical polymerization) of the monomer to proceed, whereby polymer chains are grown on the metal surface. Further, the metal surface may be covered with a transparent cover of glass, PET, polycarbonate or other materials, followed by irradiating the covered surface with light (e.g. ultraviolet light) as described hereinabove. The solvent for application (spraying), the method for application (spraying), the method for immersion, the conditions for irradiation, and the like may be the materials or methods described hereinabove. Moreover, similarly to the above, when polymer chains are formed on a metal plate, the duration of irradiation with ultraviolet light having a wavelength of, for example, 300 to 400 nm for one polymer chain forming step may be reduced to 3 to 120 minutes, 5 to 100 minutes, or 10 to 80 minutes. When polymer chains are formed on a guide wire, the duration of light irradiation for one polymer chain forming step may be reduced to 10 to 1000 minutes, 60 to 800 minutes, or 100 to 600 minutes.

In step 3 and step II, two or more types of monomers may be radically polymerized simultaneously. Moreover, multiple types of polymer chains may be grown on the metal surface. Furthermore, the polymer chains may be crosslinked to one another. In this case, the polymer chains may be crosslinked to one another by ionic crosslinking, crosslinking by a hydrophilic group containing an oxygen atom, or crosslinking by a halogen group such as iodine.

After step 3 or step II, the methods may include performing, at least once: a step of adsorbing a hydrogen abstraction type photopolymerization initiator onto the surface and then polymerizing a monomer in the presence of an alkali metal salt; or a step of polymerizing a monomer in the presence of a hydrogen abstraction type photopolymerization initiator and an alkali metal salt. Each step may be carried out in the same manner as in, for example, step 2, step 3, or step II.

The above-described modification methods may be applied to at least a part of a three-dimensional solid body to produce a surface-modified three-dimensional metal with modified properties. Preferred examples include polymer brushes. The term "polymer brush" means an assembly of graft polymer molecules obtained in the "grafting from" approach by surface-initiated polymerization. The graft chains are preferably oriented in a direction substantially vertical to the surface of the modified object because then the entropy decreases to reduce the molecular mobility of the graft chains, thereby providing lubricity. Furthermore, semidilute or concentrated brushes having a brush density of 0.01 chains/nm$^2$ or higher are preferred.

The surface modification methods may be used to produce medical devices at least partially having a modified surface. The modification is preferably applied to the surface of medical devices at least at a portion that requires lubricity, and may be applied to the entire surface.

The surface-modified metals of the present invention have lubricity imparted to the metal surface, and further have improved durability of the lubricant layer on the metal surface and therefore reduced deterioration in the sliding properties of the metal. Such surface-modified metals can be suitably used for, for example, metal medical devices, e.g. guide wires, syringe needles, metal tubes in medical devices or equipment, and other medical devices.

EXAMPLES

The present invention is more specifically described with reference to examples below, but is not limited only to these examples.

Example 1

The surface of a SUS flat plate (10 cm square, 1 mm in thickness) was washed with acetone and dried.

The plate was immersed in a 2% by mass aqueous solution of (3-acryloyloxypropyl)trimethoxysilane containing 2% by mass of acetic acid for 10 minutes, taken out and dried for 24 hours. The plate was then washed with acetone. The treated SUS plate was immersed in a 1% by mass solution of benzophenone in acetone, taken out and dried.

On the surface of the dried SUS plate was dropped an aqueous solution of 2-(methacroyloxy) ethyl trimethylammonium chloride (1.25 M) containing sodium chloride adjusted at a concentration of 1.5 M. Then, the surface was covered with a 1 mm thick glass plate, and the covered surface was irradiated with LED-UV (5 mW/cm$^2$) having a wavelength of 365 nm for 60 minutes to cause surface-initiated radical polymerization. Subsequently, the surface was washed with water to wash away unreacted monomer and the like. In this manner, a surface-modified metal was prepared.

Example 2

The surface of a SUS flat plate (10 cm square, 1 mm in thickness) was washed with acetone and dried.

The plate was immersed in a 2% by mass aqueous solution of (3-acryloyloxypropyl)trimethoxysilane containing 2% by mass of acetic acid for 10 minutes, taken out and dried for 24 hours. The plate was then washed with acetone. The treated SUS plate was immersed in a 1% by mass solution of benzophenone in acetone, taken out and dried.

On the surface of the dried SUS plate was dropped an aqueous solution of 2-(methacroyloxy)ethyl trimethylammonium chloride (1.25 M) containing potassium chloride adjusted at a concentration of 0.75 M. Then, the surface was covered with a 1 mm thick glass plate, and the covered surface was irradiated with LED-UV (5 mW/cm$^2$) having a wavelength of 365 nm for 60 minutes to cause surface-initiated radical polymerization. Subsequently, the surface was washed with water to wash away unreacted monomer and the like. In this manner, a surface-modified metal was prepared.

Example 3

The treatment with a silane coupling agent, benzophenone treatment, and drying were carried out in the same manner as in Example 1, except that the SUS plate was changed to a SUS guide wire (core wire).

Subsequently, the dried guide wire was put in a glass vessel containing an aqueous solution of 2-(methacroyloxy) ethyl trimethylammonium chloride (1.25 M) containing sodium chloride adjusted at a concentration of 1.5 M, and the vessel was sealed with a stopper. After argon substitution was performed for two hours to remove oxygen, the glass vessel was irradiated with LED-UV (5 mW/cm$^2$) for 480 minutes while being rotated, to cause surface-initiated radical polymerization. In this manner, a surface-modified metal was prepared.

Example 4

A surface-modified metal was prepared by carrying out surface-initiated radical polymerization in the same manner as in Example 3, except that the SUS guide wire (core wire) was changed to a nickel-titanium alloy guide wire.

Example 5

The surface of a SUS guide wire (core wire) was washed with acetone and dried.

The guide wire was immersed in a 2% by mass aqueous solution of (3-acryloyloxypropyl)trimethoxysilane containing 2% by mass of acetic acid for 10 minutes, taken out and dried for 24 hours. The guide wire was then washed with acetone. The treated SUS guide wire was immersed in a 1% by mass solution of benzophenone in acetone, taken out and dried.

The dried SUS guide wire was put in a glass vessel containing an aqueous solution containing acrylic acid and sodium chloride adjusted at concentrations of 2.5 M and 1.5 M, respectively, and the vessel was sealed with a stopper. After argon substitution was performed for two hours to remove oxygen, the glass vessel was irradiated with LED- UV (5 mW/cm$^2$) having a wavelength of 365 nm for 480 minutes while being rotated, to cause surface-initiated radical polymerization.

Subsequently, the surface was washed with water and dried, and then the guide wire was immersed in a 1% by mass solution of benzophenone in acetone, taken out and dried.

The dried guide wire was put in a glass vessel containing an aqueous solution of 2-(methacroyloxy)ethyl trimethylammonium chloride (1.25 M) containing sodium chloride adjusted at a concentration of 1.5 M, and the vessel was sealed with a stopper. After argon substitution was performed for two hours to remove oxygen, the glass vessel was irradiated with LED-UV (5 mW/cm$^2$) having a wavelength of 365 nm for 480 minutes while being rotated, to cause surface-initiated radical polymerization. Subsequently, the surface was washed with water to wash away unreacted monomer and the like. In this manner, a surface-modified metal was prepared.

Example 6

The surface of a SUS guide wire (core wire) was washed with acetone and dried.

The guide wire was immersed in a 2% by mass aqueous solution of (3-acryloyloxypropyl)trimethoxysilane containing 2% by mass of acetic acid for 10 minutes, taken out and dried for 24 hours. The guide wire was then washed with acetone. The treated SUS guide wire was immersed in a 1% by mass solution of benzophenone in acetone, taken out and dried.

The dried SUS guide wire was put in a glass vessel containing an aqueous solution containing acrylic acid and potassium chloride adjusted at concentrations of 2.5 M and 0.75 M, respectively, and the vessel was sealed with a stopper. After argon substitution was performed for two hours to remove oxygen, the glass vessel was irradiated with LED-UV (5 mW/cm$^2$) having a wavelength of 365 nm for 480 minutes while being rotated, to cause surface-initiated radical polymerization.

Subsequently, the surface was washed with water and dried, and then the guide wire was immersed in a 1% by mass solution of benzophenone in acetone, taken out and dried.

The dried guide wire was put in a glass vessel containing an aqueous solution of 2-(methacroyloxy)ethyl trimethylammonium chloride (1.25 M) containing potassium chloride adjusted at a concentration of 0.75 M, and the vessel was sealed with a stopper. After argon substitution was performed for two hours to remove oxygen, the glass vessel was irradiated with LED-UV (5 mW/cm$^2$) having a wavelength of 365 nm for 960 minutes while being rotated, to cause surface-initiated radical polymerization. Subsequently, the surface was washed with water to wash away unreacted monomer and the like. In this manner, a surface-modified metal was prepared.

Example 7

The surface of a SUS guide wire (core wire) was washed with acetone and dried.

The guide wire was immersed in a 2% by mass aqueous solution of (3-acryloyloxypropyl)trimethoxysilane containing 2% by mass of acetic acid for 10 minutes, taken out and dried for 24 hours. The guide wire was then washed with acetone. The treated SUS guide wire was immersed in a 1% by mass solution of benzophenone in acetone, taken out and dried.

The dried SUS guide wire was put in a glass vessel containing an aqueous solution containing acrylamide and sodium chloride adjusted at concentrations of 2.5 M and 1.5 M, respectively, and the vessel was sealed with a stopper. After argon substitution was performed for two hours to remove oxygen, the glass vessel was irradiated with LED-UV (5 mW/cm$^2$) having a wavelength of 365 nm for 800 minutes while being rotated, to cause surface-initiated radical polymerization.

Subsequently, the surface was washed with water and dried, and then the guide wire was immersed in a 1% by mass solution of benzophenone in acetone, taken out and dried.

The dried guide wire was put in a glass vessel containing an aqueous solution of 2-(methacroyloxy)ethyl trimethylammonium chloride (1.25 M) containing sodium chloride adjusted at a concentration of 1.5 M, and the vessel was sealed with a stopper. After argon substitution was performed for two hours to remove oxygen, the glass vessel was irradiated with LED-UV (5 mW/cm$^2$) having a wavelength of 365 nm for 480 minutes while being rotated, to cause surface-initiated radical polymerization. Subsequently, the surface was washed with water to wash away unreacted monomer and the like. In this manner, a surface-modified metal was prepared.

Example 8

A surface-modified metal was prepared in the same manner as in Example 5, except that the monomer used in the second polymerization was changed from the aqueous solution of 2-(methacroyloxy) ethyl trimethylammonium chloride (1.25 M) to an aqueous solution of potassium 3-sulfopropyl methacrylate (1.25 M), and the duration of irradiation with LED-UV (5 mW/cm$^2$) having a wavelength of 365 nm was changed from 480 minutes to 720 minutes.

Example 9

A surface-modified metal was prepared in the same manner as in Example 8, except that the monomer used in the second polymerization was changed from the aqueous solution of potassium 3-sulfopropyl methacrylate (1.25 M) to an aqueous solution of 2-methacryloyloxyethyl phosphorylcholine (1.25 M).

Example 10

A surface-modified metal was prepared in the same manner as in Example 8, except that the monomer used in the second polymerization was changed from the aqueous solution of potassium 3-sulfopropyl methacrylate (1.25 M) to [2-(methacryloyloxy)ethyl]dimethyl-(3-sulfopropyl) aminium hydroxide (1.25 M).

Example 11

The surface of a SUS flat plate (10 cm square, 1 mm in thickness) was washed with acetone and dried.

The plate was immersed in a 2% by mass solution of (3-acryloyloxypropyl)trimethoxysilane containing 2% by mass of acetic acid for 10 minutes, taken out and dried for 24 hours. The plate was then washed with acetone.

On the surface of the dried SUS plate was dropped an aqueous solution of 2-(methacroyloxy)ethyl trimethylammonium chloride (1.25 M) containing sodium chloride and benzophenone adjusted at concentrations of 1.5 M and 0.003 M, respectively. Then, the surface was covered with a 1 mm thick glass plate, and the covered surface was irradiated with LED-UV (5 mW/cm$^2$) having a wavelength of 365 nm for 180 minutes to cause surface-initiated radical polymerization. Subsequently, the surface was washed with water to wash away unreacted monomer and the like. In this manner, a surface-modified metal was prepared.

Comparative Example 1

The surface of a SUS flat plate (10 cm square, 1 mm in thickness) was washed with acetone and dried before use.

Comparative Example 2

A SUS guide wire (core wire) was washed with acetone and dried before use.

Comparative Example 3

A nickel-titanium alloy guide wire (core wire) was washed with acetone and dried before use.

Comparative Example 4

The surface of a SUS flat plate (10 cm square, 1 mm in thickness) was washed with acetone and dried.

The plate was immersed in a 2% by mass aqueous solution of (3-acryloyloxypropyl)trimethoxysilane containing 2% by mass of acetic acid for 10 minutes, taken out and dried for 24 hours. The plate was then washed with acetone. The treated SUS plate was immersed in a 1% by mass solution of benzophenone in acetone, taken out and dried.

On the surface of the dried SUS plate was dropped an aqueous solution of 2-(methacroyloxy) ethyl trimethylammonium chloride (1.25 M). Then, the surface was covered with a 1 mm thick glass plate, and the covered surface was irradiated with LED-UV (5 mW/cm$^2$) having a wavelength of 365 nm for 360 minutes to cause surface-initiated radical polymerization. Subsequently, the surface was washed with water to wash away unreacted monomer and the like. In this manner, a surface-modified metal was prepared.

Comparative Example 5

The surface of a SUS guide wire (core wire) was washed with acetone and dried.

The guide wire was immersed in a 2% by mass aqueous solution of (3-acryloyloxypropyl)trimethoxysilane containing 2% by mass of acetic acid for 10 minutes, taken out and dried for 24 hours. The guide wire was then washed with acetone. The treated SUS guide wire was immersed in a 1% by mass solution of benzophenone in acetone, taken out and dried.

The resulting SUS guide wire was put in a glass vessel containing an aqueous solution of acrylic acid (2.5 M), and the vessel was sealed with a stopper. After argon substitution was performed for two hours to remove oxygen, the glass vessel was irradiated with LED-UV (5 mW/cm$^2$) having a wavelength of 365 nm for 2,880 minutes while being rotated, to cause surface-initiated radical polymerization.

Subsequently, the surface was washed with water and dried, and then the guide wire was immersed in a 1% by mass solution of benzophenone in acetone, taken out and dried.

The dried guide wire was put in a glass vessel containing an aqueous solution of 2-(methacroyloxy)ethyl trimethylammonium chloride (1.25 M), and the vessel was sealed with a stopper. After argon substitution was performed for two hours to remove oxygen, the glass vessel was irradiated with LED-UV (5 mW/cm$^2$) having a wavelength of 365 nm for 2,880 minutes while being rotated, to cause surface-initiated radical polymerization. Subsequently, the surface was washed with water to wash away unreacted monomer and the like. In this manner, a surface-modified metal was prepared.

Comparative Example 6

The surface of a SUS flat plate (10 cm square, 1 mm in thickness) was washed with acetone and dried.

The plate was immersed in a 2% by mass aqueous solution of (3-acryloyloxypropyl)trimethoxysilane containing 2% by mass of acetic acid for 10 minutes, taken out and dried for 24 hours. The plate was then washed with acetone.

On the surface of the dried SUS plate was dropped an aqueous solution of 2-(methacroyloxy) ethyl trimethylammonium chloride (1.25 M) containing benzophenone adjusted at a concentration of 0.003 M. Then, the surface was covered with a 1 mm thick glass plate, and the covered surface was irradiated with LED-UV (5 mW/cm$^2$) having a wavelength of 365 nm for 180 minutes to cause surface-initiated radical polymerization.

Subsequently, the surface was washed with water to wash away unreacted monomer and the like. In this manner, a surface-modified metal was prepared.

The surface-modified metals, flat plates, and guide wires were evaluated for sliding properties in the following way.

<Evaluation of Sliding Properties>

The surface-modified metals, flat plates, and guide wires were watered and rubbed by a hand to subjectively evaluate sliding properties.

(Evaluation Results)

The surfaces of Comparative Examples 1, 2, and 3 were found not to be slippery but to have a feel like their original metal surface and thus have low sliding properties. In contrast, the surfaces of Examples 1 to 4, and 11 were slippery and had significantly improved sliding properties. The surfaces of Comparative Examples 4 to 6 were slippery but less slippery than the surfaces of Examples 1, 6, and 11, respectively. The surfaces of Examples 5 to 7 were more slippery than the surface of Example 3. The surfaces of Examples 8 to 10 were as slippery as the surface of Example 5.

In addition, the surfaces of Examples 1 to 11 remained slippery and showed no change in sliding properties after rubbing 100 times by a hand. These results demonstrate that the surface-modified metals of the examples have good sliding properties (lubricity) and further have excellent durable sliding properties.

The invention claimed is:

1. A surface-modified metal, at least partially having a treated surface, the treated surface being obtained by treating a surface of a metal with a silane coupling agent, followed by adsorbing a hydrogen abstraction type photopolymerization initiator onto the surface and then polymerizing a monomer in the presence of an alkali metal salt.

2. The surface-modified metal according to claim 1,
wherein the treated surface is obtained by, after adsorbing the hydrogen abstraction type photopolymerization initiator onto the surface and then polymerizing the monomer in the presence of the alkali metal salt, further performing the following step at least once: polymerizing a monomer in the presence of a hydrogen abstraction type photopolymerization initiator and an alkali metal salt; or adsorbing a hydrogen abstraction type photopolymerization initiator onto the surface and then polymerizing a monomer in the presence of an alkali metal salt.

3. A surface-modified metal, at least partially having a treated surface, the treated surface being obtained by treating a surface of a metal with a silane coupling agent, followed by polymerizing a monomer in the presence of a hydrogen abstraction type photopolymerization initiator and an alkali metal salt.

4. The surface-modified metal according to claim 3,
wherein the treated surface is obtained by, after polymerizing the monomer in the presence of the hydrogen abstraction type photopolymerization initiator and the alkali metal salt, further performing the following step at least once: polymerizing a monomer in the presence of a hydrogen abstraction type photopolymerization initiator and an alkali metal salt; or adsorbing a hydrogen abstraction type photopolymerization initiator onto the surface and then polymerizing a monomer in the presence of an alkali metal salt.

5. The surface-modified metal according to claim 1,
wherein the monomer is at least one selected from the group consisting of hydrophilic monomers, alkali metal-containing monomers, and halogen-containing monomers.

6. The surface-modified metal according to claim 1,
wherein the silane coupling agent is a vinyl group-containing compound.

7. The surface-modified metal according to claim 1,
wherein the metal to be treated is stainless steel or a nickel-titanium alloy.

8. A medical device, comprising the surface-modified metal according to claim 1.

9. The medical device according to claim 8, which is a guide wire, a syringe needle, or a tube of a medical instrument.

10. A method for modifying a metal surface, the method comprising:
step 1 of treating a metal surface with a silane coupling agent;
step 2 of adsorbing a hydrogen abstraction type photopolymerization initiator onto the metal surface treated in the step 1 to form polymerization initiation points; and
step 3 of polymerizing a monomer starting from the polymerization initiation points in the presence of an alkali metal salt to grow polymer chains on the metal surface.

11. A method for modifying a metal surface, the method comprising:
step I of treating a metal surface with a silane coupling agent; and
step II of polymerizing a monomer in the presence of a hydrogen abstraction type photopolymerization initiator and an alkali metal salt on the metal surface treated in the step I to grow polymer chains on the metal surface.

12. The method according to claim 10,
wherein after the step 3, the method comprises performing, at least once: a step of adsorbing a hydrogen abstraction type photopolymerization initiator onto the surface and then polymerizing a monomer in the presence of an alkali metal salt; or a step of polymerizing a monomer in the presence of a hydrogen abstraction type photopolymerization initiator and an alkali metal salt.

13. The method according to claim 11,
wherein after the step II, the method comprises performing, at least once: a step of adsorbing a hydrogen abstraction type photopolymerization initiator onto the surface and then polymerizing a monomer in the presence of an alkali metal salt; or a step of polymerizing a monomer in the presence of a hydrogen abstraction type photopolymerization initiator and an alkali metal salt.

* * * * *